United States Patent
Pratt

(10) Patent No.: US 8,100,851 B2
(45) Date of Patent: Jan. 24, 2012

(54) APPARATUS AND METHOD FOR CLEANING A SURGICALLY PREPARED BONE SURFACE

(75) Inventor: William Ralph Pratt, Newbury Park, CA (US)

(73) Assignee: Kinamed, Inc., Camarillo, CA (US)

( * ) Notice: Subject to any disclaimer, the term of this patent is extended or adjusted under 35 U.S.C. 154(b) by 1340 days.

(21) Appl. No.: 11/363,462

(22) Filed: Feb. 27, 2006

(65) Prior Publication Data

US 2006/0142690 A1    Jun. 29, 2006

Related U.S. Application Data

(63) Continuation-in-part of application No. 10/941,313, filed on Sep. 15, 2004, now abandoned.

(51) Int. Cl.
*A61M 37/00* (2006.01)
(52) U.S. Cl. .......................................... 604/23
(58) Field of Classification Search .................... 604/23, 604/118, 19, 26, 27, 28, 35, 39, 43, 49, 54, 604/268, 289, 290, 310, 313, 315, 355, 902
See application file for complete search history.

(56) References Cited

U.S. PATENT DOCUMENTS

| | | | |
|---|---|---|---|
| 5,037,437 A | 8/1991 | Matsen, III | 623/16 |
| 5,554,111 A * | 9/1996 | Morrey et al. | 604/26 |
| 6,386,865 B1 * | 5/2002 | Suh et al. | 433/27 |
| 6,960,182 B2 * | 11/2005 | Moutafis et al. | 604/43 |
| 2005/0159765 A1 * | 7/2005 | Moutafis et al. | 606/167 |
| 2006/0058730 A1 * | 3/2006 | Pratt et al. | 604/26 |

OTHER PUBLICATIONS

"Carbojet Co, Lavage System", Kinamed, Inc., Nov. 1, 2003, pp. 1-4.

* cited by examiner

*Primary Examiner* — Jackie Ho
*Assistant Examiner* — Michael J Anderson
(74) *Attorney, Agent, or Firm* — Koppel, Patrick, Heybl & Philpott

(57) ABSTRACT

An apparatus suitable for cleaning a surgically prepared working surface comprises a body portion adapted to supply pressurized fluid (preferably carbon dioxide gas) to the surgically prepared working surface and aspirate surface debris dislodged from the surgically prepared working surface. The apparatus further comprises a head portion adapted to constrain the supplied pressurized fluid to flow substantially along the surgically prepared working surface to dislodge debris there from when the head portion is in contact with the surgically prepared working surface. The dislodged surface debris are aspirated by the body portion. A second embodiment includes a Venturi-assisted cleaning head and is operable with or without an external source of vacuum.

14 Claims, 6 Drawing Sheets

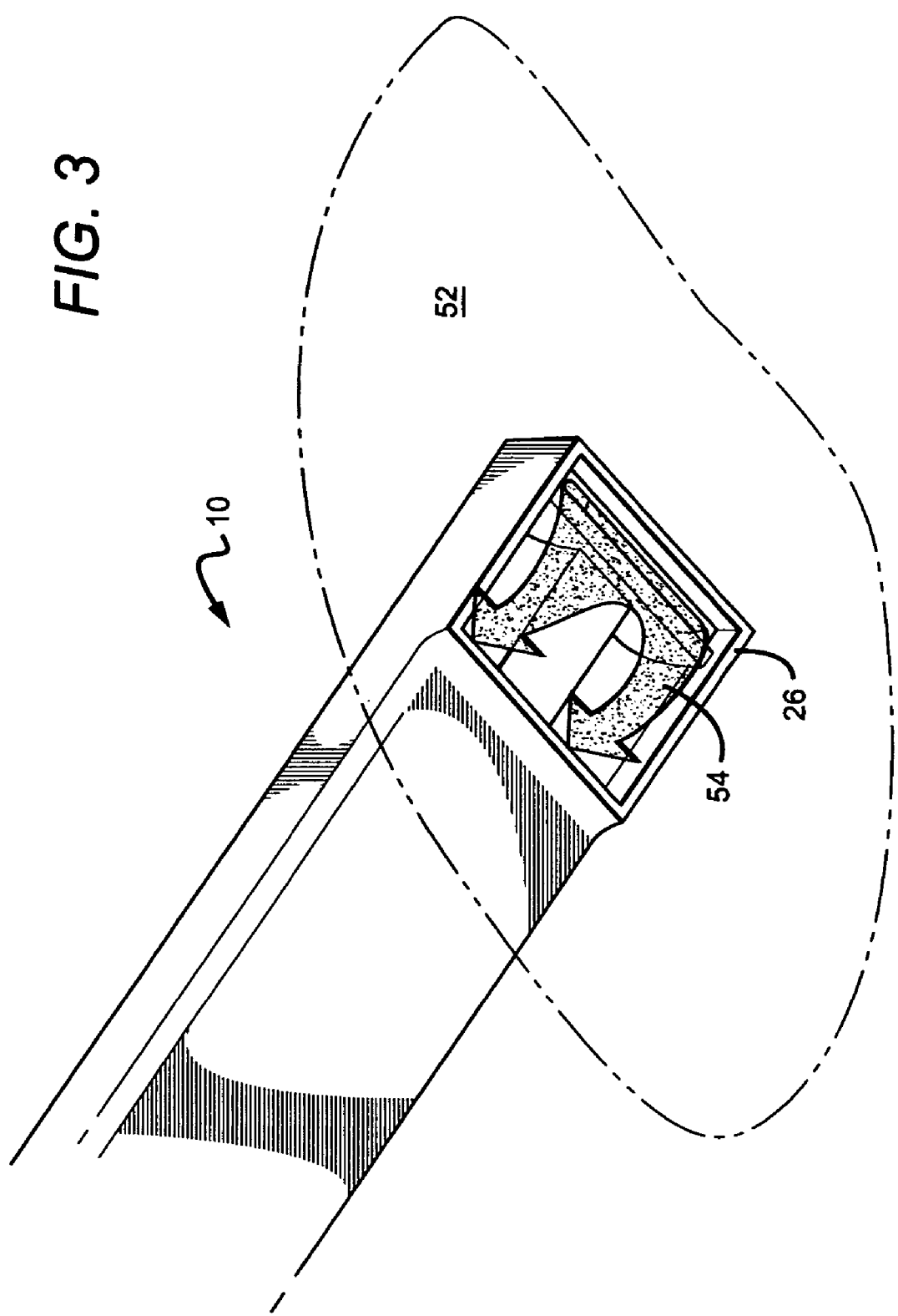

APPARATUS AND METHOD FOR CLEANING A SURGICALLY PREPARED BONE SURFACE

This application is a Continuation-in-part of U.S. application Ser. No. 10/941,313 filed on 15 Sep. 2004, now abandoned and claims priority of that application as to all matter disclosed therein.

BACKGROUND OF THE INVENTION

1. Field of the Invention

The present invention relates generally to surgical instruments, and more particularly to apparatus and method for cleaning a surgically prepared working surface.

2. Description of the Related Art

In traditional orthopedic surgery, bone is prepared to receive a prosthetic implant by first cutting or sculpting the bone with a manual or powered tool such as a saw, drill, or broach. Next, the exposed bone is usually cleaned with a sterile saline solution for lavage and irrigation. Finally, suction is applied to remove debris. Often, surgical sponges are inserted into a cavity or against the bone surface to absorb excess fluids.

Joint replacements are commonly but not necessarily secured with the aid of "joint cement" or biocompatible adhesives. A typical such cement is a polymethyl methacrylate. The success of such adhesives is thought to depend in part on proper preparation of the bone bed.

U.S. Pat. No. 5,037,437 to Matsen III (1991) discloses a significant improvement in the art of preparing bone surface for cemented joint replacement surgery. Matsen identified some of the previously unrecognized shortcomings of traditional liquid flushing lavage for preparation of the cancellous portions of an exposed bone bed. Matsen's invention was based on the finding that dry flowing gas directed at and into the sculpted bony bed effectively prepares the bone for prosthetic implantation. When a bone cement is also used, the use of gas increases the likelihood of strong mechanical interdigitation of the bone cement with the bone. A number of such advantages to the gas lavage technique are identified in U.S. Pat. No. 5,037,437; the enumerated advantages need not be repeated here. Additional advantages may exist which have not been identified. Matsen also suggests that carbon dioxide is especially well suited for use as the dry gas for bone lavage, being demonstrated safe for use in the human body. As he notes, "the very high diffusion coefficient of carbon dioxide causes it to present a significantly lower risk of embolism as compared to the use of nitrogen or oxygen." Moreover, carbon dioxide gas is commonly available in hospital operating rooms, finding use in laparascopic surgery, for example.

Since the publication of the Matsen patent, tools have become available for preparing bony surfaces by sterile, dry gas lavage, or lavage with sterile admixtures of gas and liquid. A carbon dioxide lavage system is available, for example, from Kinamed, Inc. in Camarillo, Calif. (marketed under the trade name "CarboJet"). The use of carbon dioxide is believed to be more effective than liquid debris removal because a compressed gas jet creates strong, fluctuating pressure gradients, displacing debris rapidly and thoroughly. This method is more effective at removing fluid and fluid-suspended debris from the interstices of cancellous bone.

Although surgical gas lavage nozzles are available, typical nozzles must be used in concert with surgical suction tools. Simultaneous manipulation and coordination of both gas supply and suction is difficult. Flow of the gas is not well controlled or confined to the bony surface. Both suction and gas jet must be constantly moved in a drying pattern to effectively clean and dry the bony surface. The difficulty of this technique in increased in surgical situations that permit only limited access or interfere with the surgeon's freedom of motion. As one example, in knee replacement surgery several planar bone cuts are commonly made in the femur and tibia It is desirable to prepare these surfaces to receive prosthetics.

Many surgeons are currently employing a "minimally invasive" surgical technique for knee replacement, which involves making only a very small incision at the front of the knee. The very small incision does not permit full freedom to access the cut bone surfaces from any arbitrary angle. In fact, a gap of less than 12 millimeters may be accessible between the prepared femur and tibia surfaces. In some cases, a gap as small as 8 millimeters may be present. Conventional gas jet instruments and suction instruments are not well suited to access the planar cuts in the knee without more exposure than that offered in minimally invasive surgical techniques.

A need persists for specially adapted lavage devices and methods which can better access bony surfaces, and which more efficiently and conveniently prepare the surfaces to receive cement or implants. Any time saved in the operating room is of great value (medically and economically) to both surgeon and patient.

SUMMARY OF THE INVENTION

In accordance with one aspect of the invention, an apparatus suitable for cleaning a surgically prepared working surface comprises means for supplying pressurized fluid to the surgically prepared working surface, at least one surface debris aspirator operatively coupled to the pressurized fluid supply means, and means for constraining the supplied pressurized fluid to flow substantially along the surgically prepared working surface. The constrained fluid flow forcibly cleans the surgically prepared working surface of biological fluids and debris.

In accordance with another aspect of the invention, an apparatus suitable for cleaning a surgically prepared working surface comprises means for supplying pressurized fluid to the surgically prepared working surface, at least one surface debris aspirator operatively coupled to the pressurized fluid supply means, and means for constraining the supplied pressurized fluid to flow substantially tangentially relative to the surgically prepared working surface. The tangential fluid flow forcibly cleans the surgically prepared working surface of biological fluids and debris.

In accordance with yet another aspect of the invention, an apparatus suitable for cleaning a surgically prepared working surface comprises a body portion adapted to supply pressurized fluid to the surgically prepared working surface and aspirate surface debris dislodged from the surgically prepared working surface. The apparatus further comprises a head portion adapted to confine the supplied pressurized fluid to flow substantially along the surgically prepared working surface to dislodge debris there from when the head portion is in contact with the surgically prepared working surface. The dislodged surface debris are aspirated by the body portion.

In accordance with still another aspect of the invention, an apparatus suitable for cleaning a surgically prepared working surface comprises a body portion adapted to supply pressurized fluid to the surgically prepared working surface and aspirate surface debris dislodged from the surgically prepared working surface. The apparatus further comprises a head portion adapted to constrain the supplied pressurized fluid to flow substantially tangentially relative to the surgically prepared working surface to dislodge debris there from when the head portion is in contact with the surgically prepared working surface. The dislodged surface debris are aspirated by the body portion.

In accordance with a further aspect of the invention, a method for cleaning a surgically prepared working surface comprises supplying pressurized fluid to the surgically prepared working surface, providing at least one surface debris aspirator, constraining the supplied pressurized fluid to flow substantially along the surgically prepared working surface, and using the constrained fluid flow to forcibly clean the surgically prepared working surface of biological fluids and debris.

In accordance with a still further aspect of the invention, a method for cleaning a surgically prepared working surface comprises supplying pressurized fluid to the surgically prepared working surface, providing at least one surface debris aspirator, constraining the supplied pressurized fluid to flow substantially tangentially relative to the surgically prepared working surface, and using the constrained tangential fluid flow to forcibly clean the surgically prepared working surface of biological fluids and debris.

In accordance with another aspect of the invention, An apparatus for cleaning a surgically prepared bone surface comprises a pressurized fluid supply channel; an aspiration channel; and a cleaning head, including at least one chamber, in communication with said aspiration channel and said fluid supply channel. The chamber has an orifice, the boundary of said orifice defining a boundary surface capable of close engagement with the prepared bone surface to substantially close said chamber. The chamber is arranged to create an internal pressure gradient between said pressurized fluid supply channel and said aspiration channel, with a path for fluid flow from the fluid supply channel to the aspiration channel. The fluid flow path for fluid flow includes at least one region in which flow is constrained to flow along the boundary surface.

In accordance with another aspect of the invention, an apparatus for cleaning a surgically prepared bone surface comprises a body portion adapted to supply fluid to the surgically prepared surface and to aspirate surface debris dislodged from the surgically prepared working surface; and a head portion having an orifice adapted to engage the surgically prepared bone surface. The body portion has a length dimension in a lengthwise direction, and the orifice is directed sidewards, in transverse relation to the lengthwise direction of the body portion.

In another embodiment, the invention includes a cleaning head wherein the head includes a primary fluid flow circuit arranged to flood and clean the working surface with pressurized fluid, and an auxiliary fluid flow circuit arranged to produce or augment a pressure gradient across the primary fluid flow circuit. The auxiliary fluid flow circuit includes a high velocity Venturi nozzle directed downstream to augment pressure gradient across the primary fluid flow circuit.

These and other aspects of the invention will become apparent from a review of the accompanying drawings and the following detailed description of the invention.

BRIEF DESCRIPTION OF THE DRAWINGS

The present invention is generally shown by way of reference to the accompanying drawings in which:

FIG. 3 schematically shows an exemplary embodiment of the present invention;

DETAILED DESCRIPTION OF THE INVENTION

Some embodiments of the invention will be described in detail with reference to the related drawings of FIGS. 1-4. Additional embodiments, features and/or advantages of the invention will become apparent from the ensuing description or may be learned by practicing the invention.

In the figures, the drawings are not to scale with like numerals referring to like features throughout both the drawings and the description.

The following description is not to be taken in a limiting sense, but is made merely for the purpose of describing the general principles of the invention.

Figure 1:
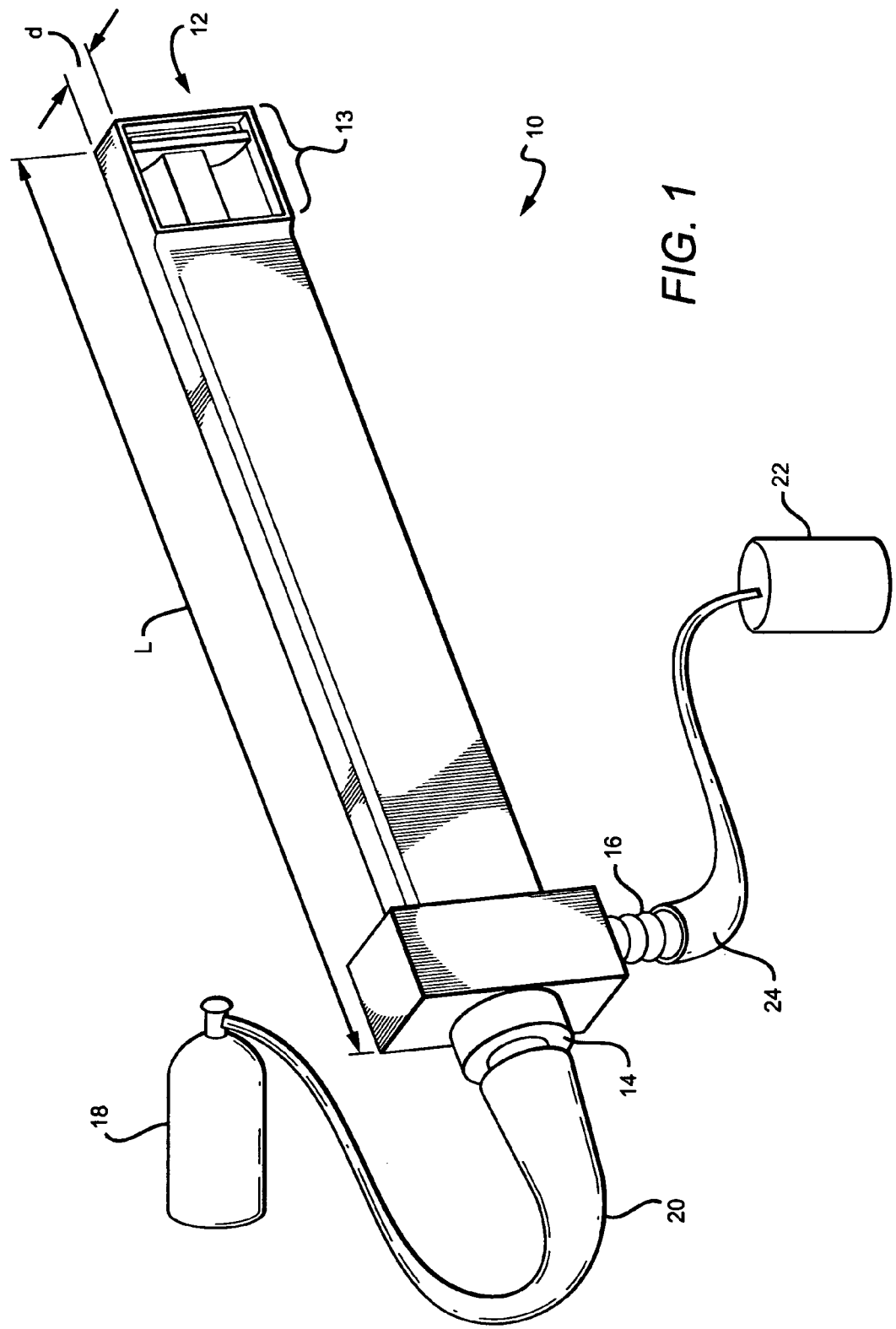
FIG. 1 is a front perspective view of an apparatus suitable for cleaning a surgically prepared working surface in accordance with the present invention.

FIG. 1 is a front perspective view of an apparatus or tool generally referred to by reference numeral 10, adapted for cleaning a surgically prepared working surface in accordance with the present invention. The embodiment of FIG. 1 is particularly well adapted for cleaning a substantially planar bony surface, such as is produced by an oscillating saw in preparation for implantation of a knee prosthesis.

The tool 10 includes an elongated body having a sidewards facing orifice 12, situated near the forward end of the body. ("Sidewards" is intended to convey that the orifice faces in a direction generally across or transverse to the long axis or dimension of the body). The forward end of the body, including the orifice, will also be referred to as the "head portion" of the tool 10 The tool preferably has hose couplings, preferably disposed near the rearward end of the tool: a pressurized gas hose connection 14 and a vacuum hose connection 16. Optionally, these connections could be integrated into a trigger type control grip (not shown) which facilitates control of the application/disconnection of both gas and suction, via a simple trigger operated valve. However controlled, gas is controllably supplied under pressure from pressurized gas supply 18 to gas connection 14 via a hose 20. Similarly, suction is controllably supplied from vacuum source 22 via hose 24 to the vacuum hose connection 16.

Figure 1A:
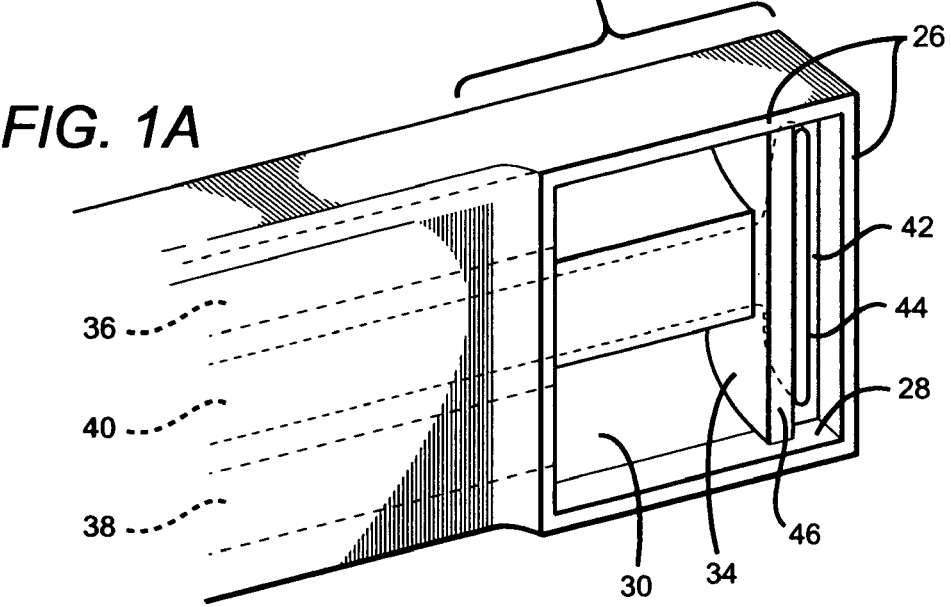
FIG. 1A is an enlarged partial front perspective view of the apparatus of FIG. 1.

The head portion 13 of tool 10 is more clearly seen in (magnified) FIG. 1A. Head 13 has an orifice 12 which is preferably bounded by a lip or rim 26. In the embodiment shown, the rim forms a generally square perimeter around the orifice 12. The orifice 12 opens into an internal cavity 26 having a forward chamber 28 and a rearward chamber 30, which are incompletely divided by an internal partition 34. At least one hidden, internal gas channels 36 and 38 connect the rearward chamber to the vacuum hose coupling 24, and thus allow the rearward chamber (vacuum chamber) 30 to communicate with the vacuum supply 22. Similarly, internal pressurized gas channel 40 connects the forward chamber 28 to the pressurized gas connection 14, allowing the forward chamber to communicate with the pressurized gas supply 18.

Forward chamber has an internal barrier 42 which is breached by a wide slot as shown. Optionally, a series of small gas directing holes could be provided to disperse the gas flow into a curtain. Such features tend to spread and direct the gas flow into a ribbon of flowing gas. Further details of the gas flow are discussed below in connection with FIG. 3.

As shown in FIG. 1A, the partition 34 does not extend completely to the plane defined by the rim 26; rather, the partition terminates in a shoulder 46 A small clearance exists between the shoulder 26 and the plane of the rim 26, defining a relatively narrow slot through which gas can flow from the forward chamber to the rearward chamber (thus from pressure toward vacuum).

The entire tool 10 can suitably be machined or otherwise formed from a solid such as aluminum or stainless steel, which are capable of enduring repeated autoclaving for sterilization. Alternatively, polymers or other materials could be used. In some embodiments the tool may be disposable, thereby avoiding the need for sterilization by the hospital.

Figure 2:
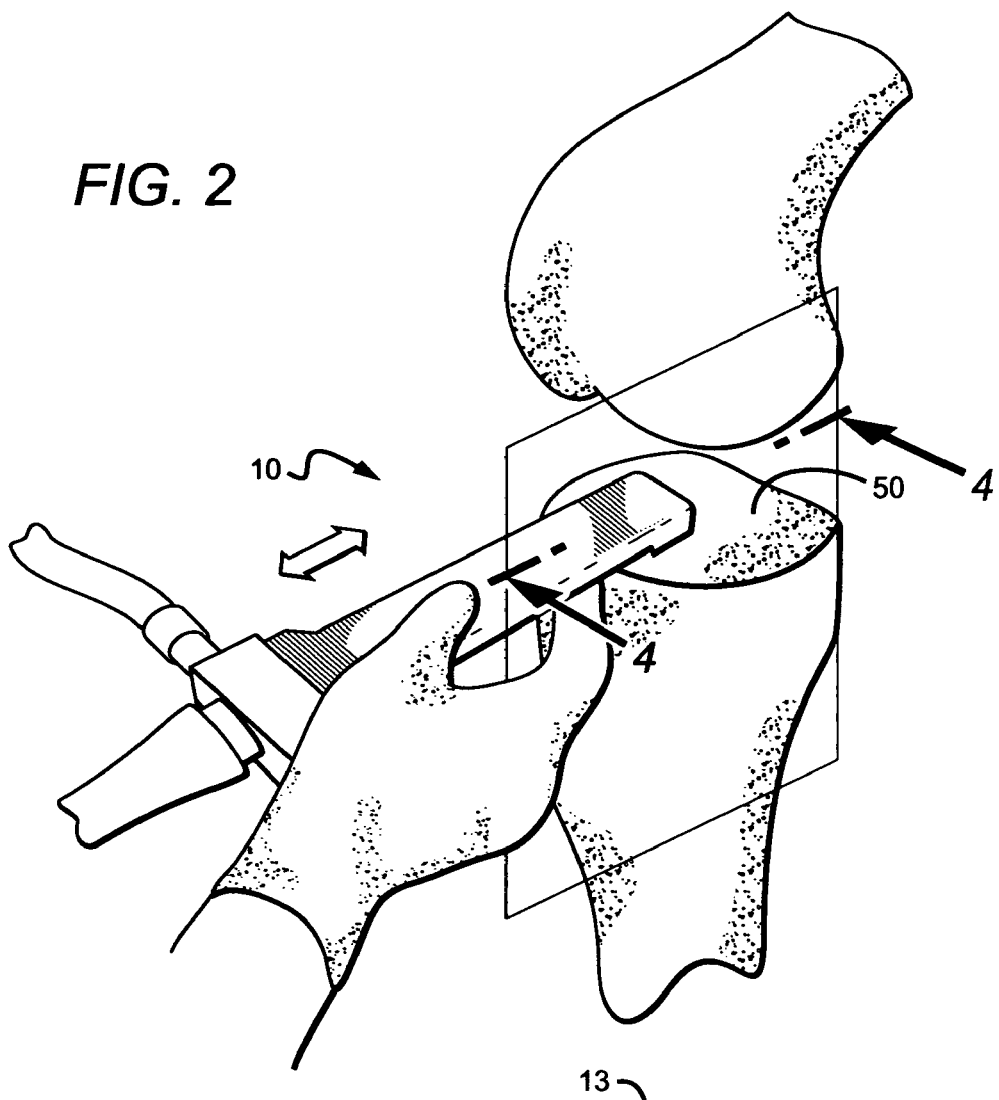
FIG. 2 is a side perspective view of the apparatus of FIG. 1 being used to clean a surgically prepared working surface in accordance with the present invention.

FIG. 2 shows how the tool can be used to prepare the bony surfaces of a knee to receive a prosthetic replacement. As shown, the bone is previously prepared by cutting with a saw to produce at least one substantially planar cut surface 50. The tool is inserted through an incision, which need not be large, and manipulated to engage the rim 26 with the planar cut, bony surface 50. A close fit is desirable, but some leakage is tolerable. Having the head of the tool engaged with the bony surface 50, the surgeon activates the sources of pressurized gas and suction, and moves the tool in a pattern to clean the bony surface. When the surface is clean (and dry), the surgeon removes the tool and applies the cement in accordance with medical practice. It is recommended that the tool be manipulated from the far side to the near side of the surface, so that debris and blood is pulled from far to near in a scraping motion.

FIG. 3 shows the direction of gas flow when the device is activated in engagement with a bony surface. The bony surface can be visualized as surface 52, but here is imagined to be transparent so as to better visualize the gas flow in the tool. The extent of the rim or other boundary of the orifice defines a boundary surface for the orifice. The FIG. assumes that the orifice is fully engaged with bony surface 52, by placing with slight pressure the rim 26 flush to the planar bone surface 52. Thus engaged, boundary surface to bony surface, the cavity and bone surface together define a substantially enclosed volume or chamber having a pressurized gas source at one end and a vacuum at the other end, incompletely separated by partition 34. More generally described, the apparatus thus engaged defines a substantially closed volume having on at least one side a bony surface. Due to the pressurized gas source and the vacuum source, the volume has a pressure gradient substantially across the bony surface. The fluid is thus constrained to flow substantially across the surgically prepared surface 52. Most preferably, in at least some region the gradient is substantially tangential to the surface to be cleaned. The fluid is constrained to flow tangentially to the surface to be cleaned, at least in some region.

In a preferred embodiment, the partition 34 constricts or pinches the gas flow, visualized by flow arrows 54 in the FIG. Flow between the partition 34 and the bony surface is pinched or constricted as the gas passes through the narrow clearance between partition and bone. Thus, across the narrow sill of partition 34 the flow has increased velocity and decreased pressure due to "Bernoulli's principle" or "venturi effect". Applicants speculate that the lowered pressure and increased velocity in this pinched channel is efficacious to draw debris and liquid (such as blood) from the interstices of a porous bony surface, which effect is observed to occur with unexpected efficiency.

Figure 4:
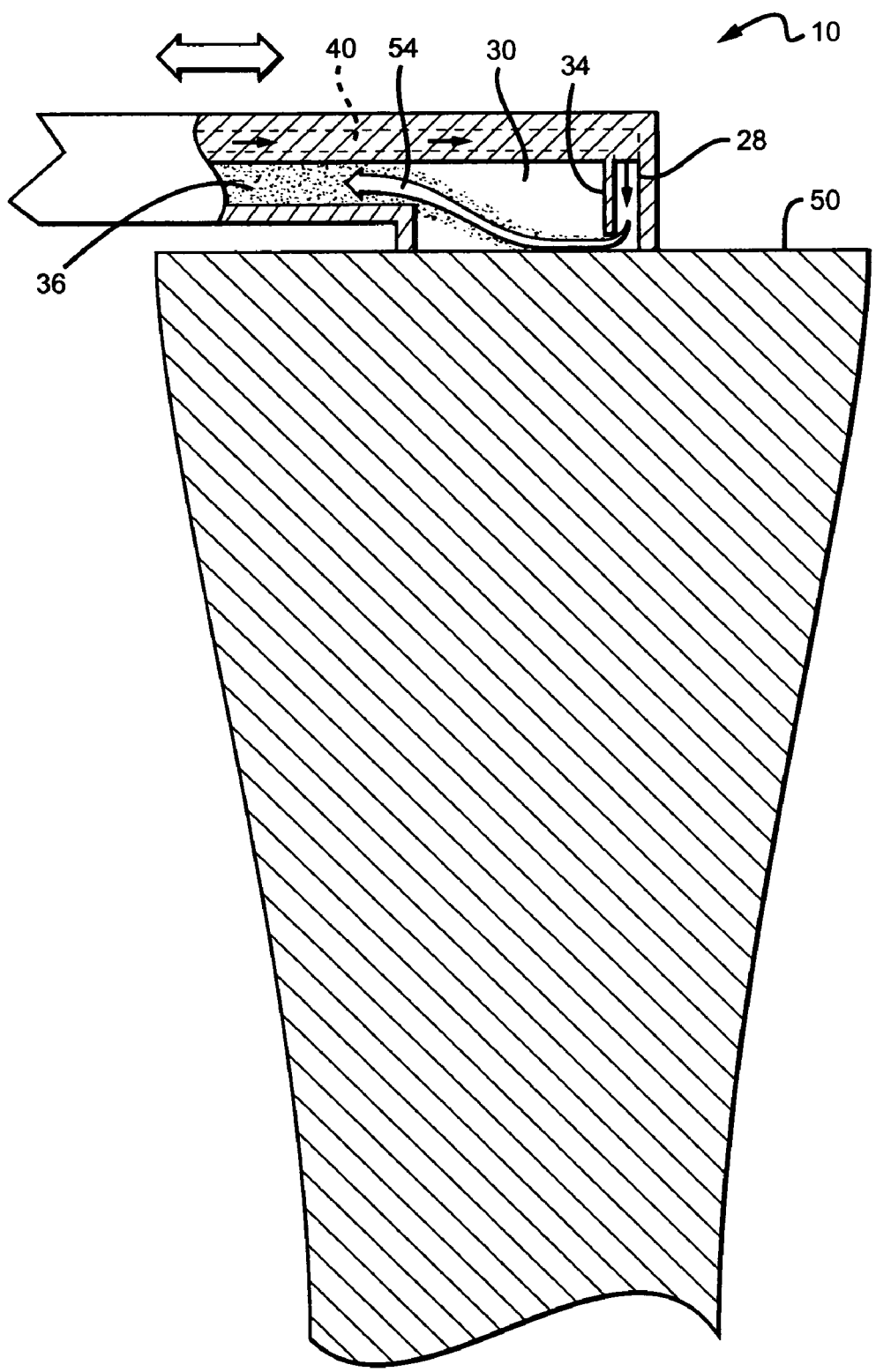
FIG. 4 is a cross-sectional view taken along the sectioning plane 4-4 of FIG. 2.

Gas flow is also visualized in FIG. 4. As the cross section shows, pressurized gas supplied from a source flows forward through an internal channel 40 in the cleaning tool 10 to the forward chamber 28. Simultaneously, suction is applied from vacuum source, which communicated via another internal channel 36 with rearward chamber 30. Due to the pressure gradient, gas flows from the forward chamber to the rearward chamber. However, the complete cavity (comprising forward and rearward chambers 28 and 30) is substantially closed when the orifice is flush against a bony surface, so the gas is constrained to flow through the relatively narrow slot between the lower sill of partition 34 and the top of the bony surface 50. In passing across this lip, the flow accelerates and the pressure drops, drawing fluid and debris off of the surface. Gas, liquid, and debris then flow into the rearward (vacuum) chamber and exit the tool through the vacuum channel, which is preferably large enough to accommodate debris without clogging. The entire cleaning process occurs within a closed volume defined by the combination of the cavity and bony surface in close fitted relationship. In addition to increasing the cleaning efficiency, the closed system also reduces splattering and controls the aerosolization of biological materials (such as blood, fat and marrow).

Although a planar geometry is shown for the orifice, other geometries could be employed for cleaning other surfaces. For example, hemispherical geometries (such as found in socket joints) could be cleaned by a tool with a suitably curved surface, provided that the orifice engage the bony surface to effectively confine the flow and encourage flow across the surface, in a direction generally tangential thereto. Furthermore, cylindrical or conical geometries could be employed to clean bone channels (such as a broached femoral canal).

Note that in the embodiment shown in the FIG.s the tool 10 has a thickness dimension d which is relatively thin in relation to its length L (indicated in FIG. 1). In some embodiments, the thickness d should preferably be less than 12 millimeters, to allow insertion through a relatively small incision into the interstices of a (prepared) knee joint. More preferably the thickness should be 8 millimeters or less, to service knee joints in a minimally invasive surgical technique. Note also that in the embodiment shown, the orifice or aperture 12 is side facing in relation to the long axis of the tool 10 and the gas and vacuum supply channels included therein. This allows easy access to surfaces having their normal disposed at substantially right angles to the long axis of the tool. This arrangement is advantageous because it considers the geometry of common cutting tools such as either circular or oscillating saws. Such saws cut planes disposed parallel to the plane of the saw's motion. The side facing orifice 12 is conveniently disposed to clean the surfaces produced by such cuts The inventors presently believe that the preferred pressurized gas for use in the invention is carbon dioxide ($CO_2$). Some of the reasons for this conclusion are set forth in the Matsen patent, referenced above in the "Background of the Invention." However, the invention could be modified to employ other pressurized gases, or an admixture of liquid and gas. In order to take full advantage of the "Bernoulli effect" in passing through the constricted channel, a compressible fluid such as a gas or gas mixture is greatly preferred.

In another embodiment (the "cleaning head with Venturi-assisted vacuum"), the nozzle of the invention includes a pressurized chamber, a collection chamber, a constrained pathway for fluid to flow between the pressurized chamber and the collection chamber across the surface to be cleaned, and an auxiliary fluid channel between the pressurized and vacuum chambers. The use and operation of the second embodiment is similar to that of the previously described and illustrated embodiment, and unless the context demands a different understanding, the remarks and description above apply to this second embodiment as well. The following description will primarily focus on the differences and unique features of the Venturi-assisted embodiment.

For ease of understanding the illustration it should be noted that in the example depicted, the cleaning head with Venturi-assisted vacuum (depicted in FIGS. 5-9) differs from the embodiment of FIGS. 1-4 in that the Venturi-assisted embodiment is illustrated with the pressurized fluid supplied through an axial channel substantially centered in an elongated tool. Unlike the previously described embodiment, the embodiment of FIGS. 5-9 is illustrated with a vacuum chamber disposed forward of the pressurized fluid supply channel, but this arrangement is not critical and variations are possible.

Figure 5:
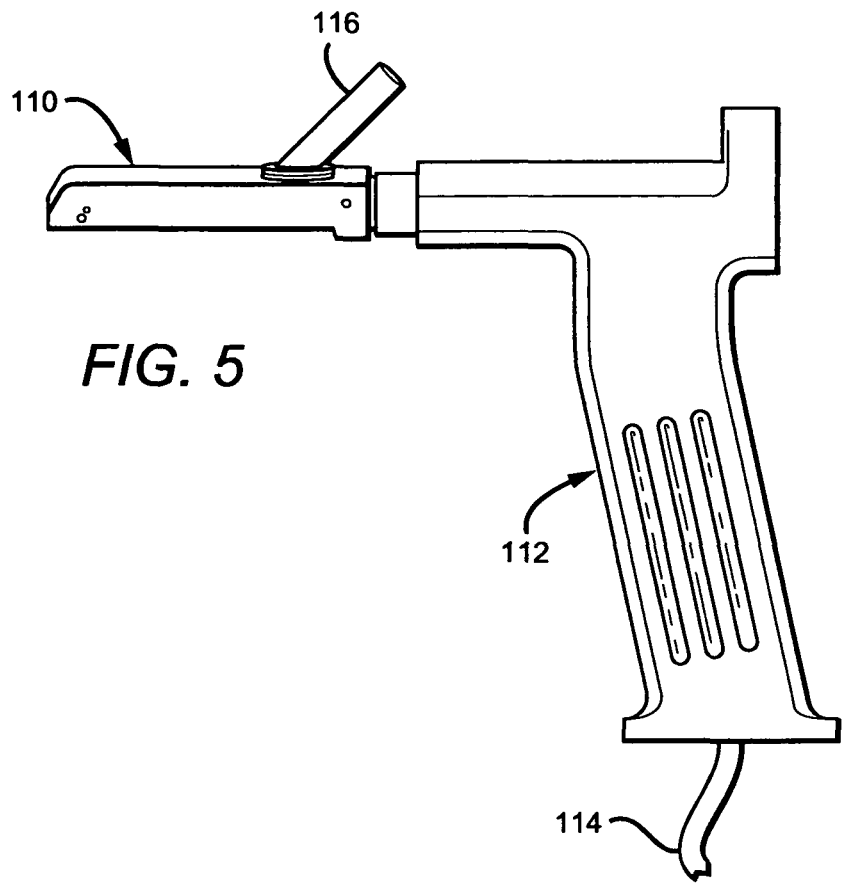
FIG. 5 is a perspective view of a second embodiment of an apparatus in accordance with the invention, mounted on a pistol grip for controlling the pressurized fluid supply.
Figure 6:
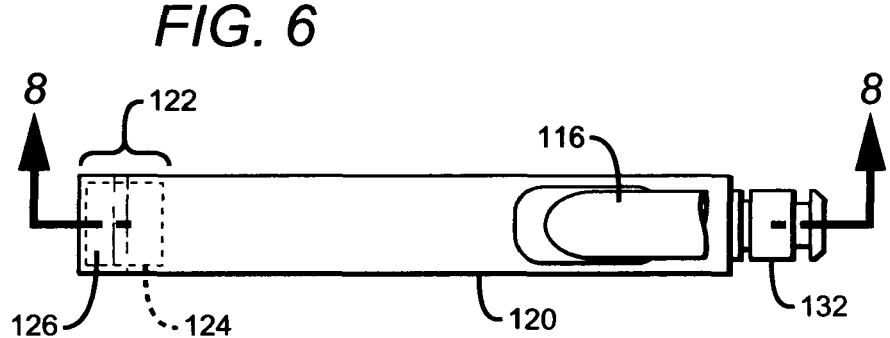
FIG. 6 is a plan view from above of the apparatus of the second embodiment.
Figure 7:
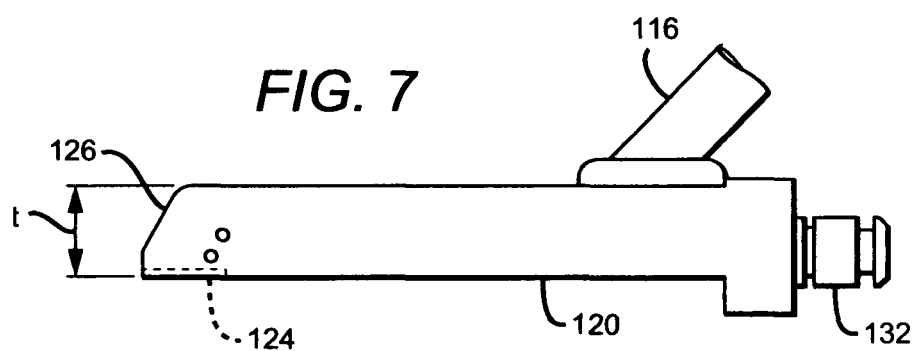
FIG. 7 is an elevation view of the apparatus of FIGS. 5 and 6.

FIG. 5 shows the venturi-assisted tool 110 mounted on a pistol-style control handle 112 through which high pressure fluid is supplied from a supply hose 114. Optionally, a trigger or pushbutton control can be included in the pistol control handle 112, allowing the operator to activate and deactivate the connection to the high-pressured fluid supply by manually activating a valve (suitably included in the control handle 112). A vacuum or aspirator outlet provided atop tool 116 is adapted to connect to a vacuum source or aspirator via a vacuum hose. Alternatively, in some embodiments this outlet 116 may be coupled to a mere collection system, as will be explained below.

Plan and elevation views (FIGS. 6 and 7, respectively) show external features of the cleaning tool. The tool includes a body 120 integrated with a forward cleaning head portion 122 having a downward facing cleaning orifice 124. A forward bevel 126 is preferably provided to facilitate manipulation of the tool into limited surgical areas, such as might be required during knee replacement surgery. As with the previously described embodiment, it is preferred that the thickness dimension t be limited to less than 11 millimeters in a tool specified for a minimally invasive knee replacement procedure. Such a tool is a particular aspect of the invention. In variants of the invention not intended for minimally invasive knee replacement surgery, a thicker tool could be used.

Figure 8:
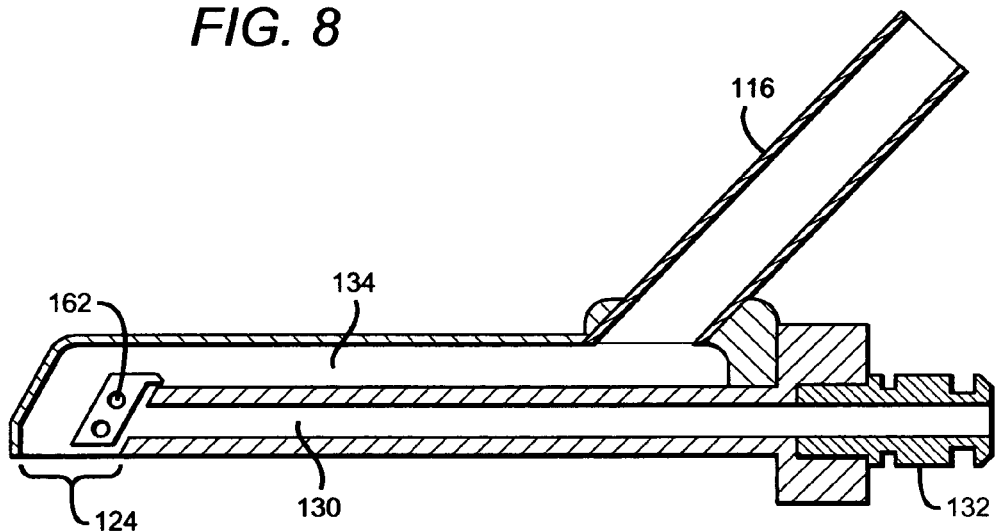
FIG. 8 is a longitudinal sectional view, taken along section line 8 in FIG. 6.

FIG. 8 shows a longitudinal sectional view of the tool, with a longitudinal section taken approximately at midsection at a plane including the axis of the pressurized fluid channel 130 The tool may suitably be bilaterally symmetrical with the section plane as the plane of symmetry, but perfect symmetry is not required. Pressurized fluid (preferably carbon dioxide gas or an admixture of gas and liquid) is supplied from the rear gas fitting 132, which would optionally be adapted to connect to a pistol grip handle 112 having a control valve (not shown in FIG. 8). Fluid under pressure is supplied through the pressurized fluid channel 130 to a forward end of the tool 110, where the cleaning orifice 124 is located. Vacuum (aspiration) is preferably also supplied from an external source or aspirator to a vacuum fitting 116. A vacuum channel 134 allows fluid flow between the tool orifice to the vacuum source. In the embodiment shown, the vacuum or aspiration channel 134 is disposed above the pressurized fluid channel 130, but other arrangements are possible. It is important that the communication between the vacuum channel 134 and the pressurized fluid channel be limited in the cleaning head 122, as discussed below.

Figure 9:
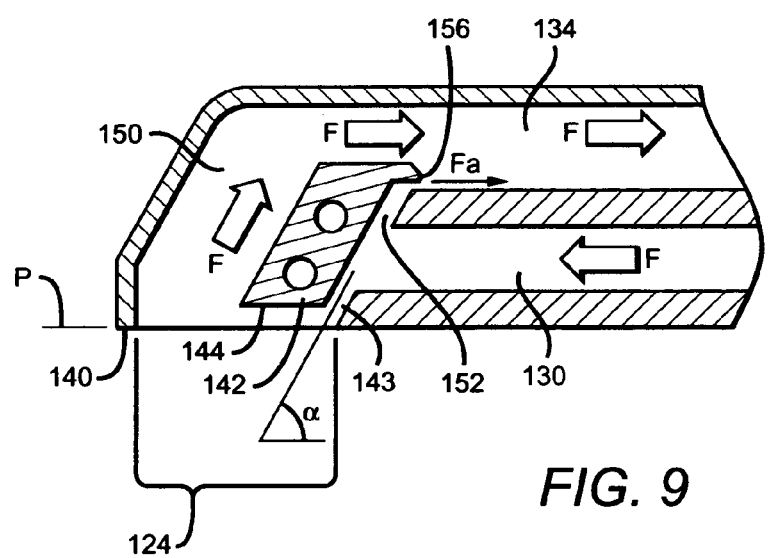
FIG. 9 is an enlarged sectional view, showing more details of the forward portion of FIG. 8, with fluid flow indicated by arrows.

The following details are more easily seen in FIG. 9, an enlarged sectional view of the head of the tool, sectioned in the same manner and along the same plane as FIG. 8 discussed above.

The cleaning orifice 124 is a downward facing opening bounded and defined by a rim 140 which provides a closed perimeter with a surface adapted to seal against the surface to be cleaned. For example, in one embodiment (as shown) a square perimeter with all rim surfaces situated on a single plane defines a square planar orifice, which is adapted to seal to a flat, generally planar surface. Such surfaces are easily produced by cutting tools such as a reciprocating saw. In another embodiment, a plane circular rim provides a circular orifice, suitable for cleaning concave surfaces such as a hemispherical concavity. More generally, the rim 140 has a contour which is adapted to closely fit to a predetermined surface shape, thus providing a seal for the cleaning orifice and confining the pressurized fluid flow inside the rim.

The cleaning head 122 includes the pressurized fluid supply channel 130, a vacuum or collection channel 134, and at least one partition 142 partially obstructing the communication between the supply channel and the collection channel. The partition preferably terminates in generally flat sill which confines a thin sheet of fluid flow between the sill and the plane of rim 140. Following the direction of fluid flow in the primary cleaning channel, fluid supplied from the high pressure fluid passage 130 is emitted from a narrow, directed slot like cleaning nozzle 143 and flows generally across the face of cleaning orifice 124. More specifically, when the cleaning orifice is effectively sealed to a work surface by pressing rim 140 to a bony surface, the fluid is constrained to flow between the work surface (plane P) as a downward boundary and the sill 144 as an upward boundary plane. Preferably sill 144 is recessed above the plane P of rim 140 by a small clearance dimension, defining the thickness of the sheet of fluid flow across the face of cleaning orifice 124. In a preferred embodiment, the clearance between sill 144 and the plane P of rim 140 is 2 millimeters or less. The angle α of the slot-like cleaning nozzle is also a factor affecting cleaning efficiency; the inventors have found that the angle alpha should preferably be between 0 and 90 degrees, inclusive, but is more preferably substantially equal to 60 degrees. This angulation tends to bias the fluid flow across the surface toward the collection chamber 150. The preferred angle (60 degrees) also permits the head to be conveniently used as a blowing nozzle, when approaching a surface but before the orifice is placed on the surface. This preferred angle provides the capability to manually alter the cleaning jet from an angled down blast (when tilted off the surface) to a flow substantially tangential to the surface (when the orifice engages the surface).

The vacuum or collection chamber 150 may suitably be larger than the pressurized fluid channel 130 and substantially larger than the constrained flow across sill 144. The increased dimensions of the collection chamber 150 allow handling of substantial debris and bodily fluid sucked from a bony surface by the orifice, passing the fluids and debris downstream toward a collection apparatus. The direction arrows F in FIG. 9 denote the general direction of fluid flow.

A significant feature of the Venturi-assisted embodiment is a narrowed or constricted auxiliary fluid pathway through auxiliary fluid channel 152 from the high pressure fluid channel 130 to the vacuum channel 134, bypassing the cleaning surface and cleaning orifice. The auxiliary flow Fa is ejected as a high-speed jet at Venturi nozzle 156 to a confluence of the primary and auxiliary flow pathways, with the Venturi nozzle 156 directed generally downstream in the direction of fluid flow. The high speed fluid jet defines a secondary fluid flow circuit bypassing the cleaning surface and cleaning orifice 124. Because the Venturi nozzle is narrowed and the jet is relatively high speed (both relative to the collection channel 134), the jet tends to lower pressure in the collection channel downstream from the cleaning orifice, thereby augmenting the vacuum at collection chamber 150 and increasing the pressure gradient across the cleaning orifice 124.

The function of the auxiliary fluid channel is to provide additional suction or aid pressure gradient in the primary cleaning circuit. The Venturi-assisted tool thus produces enhanced vacuum by the same principal that is involved in a Venturi vacuum generator or a common water aspirator: lowering of pressure by Venturi effect responsive to the high speed jet produced by the auxiliary fluid flow channel. The enhanced vacuum is effective to enhance the cleaning action of the main cleaning orifice.

Preferably the auxiliary channel should be more narrow in cross section than the collection chamber 150 and the collection channel 134, to produce a high speed Venturi jet that will efficiently augment the pressure gradient in the cleaning head.

Cleaning action of the main orifice is also aided by Venturi effect in the primary fluid flow circuit (across the surgically prepared, bony surface). The primary fluid flow circuit passes through a constrained or narrowed region of flow (between sill 144 and the bony surface) flowing substantially across a portion of the work surface to be cleaned. In the region below the sill 144, the fluid is constrained to pass as a ribbon or sheet, at high speed (hence at low pressure) between the sill 144 and the work surface (plane P). Because of the low pressure in this region, ambient pressure urges the tool toward the bony work surface which assists in sealing the rim in contact with the bony surface. Furthermore, the low pressure across a substantial region of the cleaning orifice tends to such fluids from the porous bony surface to be cleaned, picking up bodily fluids and debris as intended. In other words, a fluid flow substantially tangential to the surface through a constrained, thin region creates a low pressure zone immediately adjacent to the fluid stream, which motivates debris into the fluid stream to remove the debris.

FIG. 9 shows the directions of fluid flow with the orifice disposed in contact with a surgically prepared bony surface 160, with primary flow labeled by arrows F and secondary flow labeled by arrows Fa.

The FIGS. 5-9 illustrate one specific geometry for the cleaning head which is suited to manufacture by milling from a generally rigid material such as aluminum, stainless steel, or a polymer. It should be understood that the tool can be assembled from multiple components in various ways: for example, a generally bilaterally symmetric variation could be manufactured, symmetrical about cut plane 8 in the figures; or a right or left side plate could be joined to a main body with milled and bored channels and cavities. In some methods of manufacture, the partition 142 may be a separate piece. Accordingly, screw holes 162 are shown as a possible method for fixing the partition 142 in the main body of the tool 110 (by insertion of through or blind screws through holes 162). Other methods of manufacture could readily be conceived by those with skill in the art. In one embodiment, the cleaning tool is fabricated from a polymer material suitable for disposal; in other recyclable embodiments, the tool could be fabricated from more durable materials capable of withstanding repeated sterilization procedures.

The illustrated embodiment assumes that an active source of vacuum aspiration will be coupled to the cleaning tool; however, it should be apparent that the device is capable of producing significant vacuum merely by the venturi action in the head, without an external aspirator. Accordingly, in some variations the invention includes a cleaning tool adapted to function without an external aspirator or vacuum source. It is advantageous that the vacuum is produced directly at the tool and in close proximity to the cleaning orifice; if the pressure gradient is otherwise produced, say at some distance from the head, fluid flow losses in tubing and channels will reduce the effectiveness of the cleaning tool, particularly when the channels and tubing are required to transport considerable blood and debris. High velocity and low pressure directly at the work surface are most effective to clean and dry a bony surface.

In a typical embodiment the device with a secondary venturi channel may be operated from a 50 pounds per square inch pressurized supply of (filtered) fluid, such as carbon dioxide gas. Fluid flows in the range of approximately 50 liters per minute are typical. It is preferred that the cleaning fluid include a significant component of filtered carbon dioxide gas, for reasons discussed above; but admixtures of gas and liquid, with or without surfactant, could also be used in some applications.

A person skilled in the art would undoubtedly recognize that other components and/or configurations may be utilized in the above-described embodiments. Moreover, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

While the invention has been described in detail with regards to several embodiments, it should be appreciated that various modifications and/or variations may be made in the invention without departing from the scope or spirit of the invention. In this regard it is important to note that practicing the invention is not limited to the applications described hereinabove. Many other applications and/or alterations may be utilized provided that such other applications and/or alterations do not depart from the intended purpose of the invention. For example, the head, orifice, and rim may be shaped to fit contours other than planar surfaces. Admixtures of gas and liquid may be used in place of a carbon dioxide gas. Various control valves and pressure regulation apparatus may be added to the cleaning head or to it's supply lines. The body may comprise primarily gas and suction lines. The cleaning head may have multiple pressure chambers and/or multiple vacuum chambers; the head could be arranged with suction forward and pressure situated rearward; pressure could be provided in a middle chamber, with gas flowing to two or more suction orifices (one forward, one rear); the pressure could be provided in a middle chamber with suction divided between right and left chambers, causing dual cleaning jets (right and left). Other such variations could be devised. A skirt can be added to or substituted for the rim around the cleaning orifice. A flexible or conformable skirt could be used.

Also, features illustrated or described as part of one embodiment can be used in another embodiment to provide yet another embodiment such that the features are not limited to the exemplary embodiments described hereinabove. Thus, it is intended that the invention cover all such embodiments and variations as long as such embodiments and variations come within the scope of the appended claims and their equivalents.

I claim:

1. An apparatus suitable for cleaning a surgically prepared working surface by lavage with a pressurized fluid or fluid admixture from a pressurized fluid supply, and to aspirate fluids and debris dislodged from the surface, said apparatus comprising:
   a head adapted to deliver pressurized fluid toward the surgically prepared working surface at an angle substantially perpendicular to said surface to dislodge debris there when said head portion is in contact with the surgically prepared working surface, said dislodged surface debris being expelled through a collection channel;
   said head having a cleaning orifice adapted to engage with the working surface;
   wherein said head includes a primary fluid flow circuit arranged to flood and clean the working surface with said pressurized fluid, and an auxiliary fluid flow circuit arranged to produce or augment a pressure gradient across said working surface when said cleaning orifice is engaged with said working surface such that said pressurized fluid is constrained to flow substantially across said surface; and
   wherein said primary fluid flow circuit comprises:
      a high pressure fluid supply nozzle adapted to deliver pressurized fluid toward the surgically prepared working surface at an angle substantially perpendicular to said surface;
      a collection chamber communicating with said collection channel; and
      a partition partially obstructing flow from said high pressure fluid supply nozzle and said collection chamber, said partition terminating in a sill recessed from said cleaning orifice and defining a relatively thin passageway between said sill and said working surface which constrains fluid to flow at an increased velocity between said fluid supply nozzle and said collection chamber when said cleaning orifice is in contact with the working surface.

2. The apparatus of claim 1, further comprising a pressurized fluid source connected to said head to supply said pressurized fluid, and a collection system coupled to said head to collect fluids and debris cleaned from the working surface.

3. The apparatus of claim 2, wherein said pressurized fluid supply provides carbon dioxide gas.

4. The apparatus of claim 1, wherein said thin passageway has a thin dimension in the range 2 millimeters or less.

5. The apparatus of claim 1, wherein said collection chamber offers less flow constraint than said thin passageway.

6. The apparatus of claim 1, further comprising an auxiliary fluid channel between said cleaning orifice and said collection chamber which terminates at a high velocity Venturi nozzle directed in the direction of fluid flow down said auxiliary fluid flow circuit to augment the pressure gradient across said working surface.

7. The apparatus of claim 6 wherein said Venturi nozzle is disposed in close proximity to said cleaning orifice to augment pressure gradient effectively.

8. The apparatus of claim 1, further comprising: an aspirator, in fluid communication with said collection channel to remove said debris and fluids.

9. A method for cleaning a surgically prepared, bony surface with a pressurized fluid, comprising the steps:
   a) supplying the pressurized fluid via a pressurized fluid supply channel and through a cleaning orifice toward a region of the surgically prepared bony surface at an angle substantially perpendicular to said surface;
   b) causing pressurized fluid to flow substantially across said region of the surgically prepared bony surface, to dislodge debris and remove undesired fluids; and
   c) causing the pressurized fluid to flow through a collection channel such that a pressure gradient is formed across said cleaning orifice such that said pressurized fluid is constrained to flow substantially across said surface and said collected debris and collected fluids flow through said collection channel;
   d) providing an auxiliary fluid channel between said pressurized fluid supply channel and said collection channel to enhance said pressure gradient, to aid flow of the pressurized fluid in step c), above;
   e) confining said pressurized fluid flow across said region of surgically prepared bony surface by a cleaning orifice disposed in contact with said surface; and
   f) accelerating said fluid flow across said prepared bony surface by constraining said flow to a thin sheet between said surface and a constraining sill, disposed above said surface by a predetermined clearance.

10. The method of claim 9 wherein said auxiliary fluid channel is a component of an auxiliary fluid flow channel bypassing the bony surface.

11. The method of claim 9, wherein said clearance is less than 2 mm.

12. The method of claim 11, wherein said orifice is bounded by a rim, said rim defining a surface predetermined to closely fit the bony surface, thereby sealing said orifice to said surface and confining said fluid flow.

13. The method of claim 9, wherein said pressurized fluid comprises carbon dioxide gas.

14. The apparatus of claim 1, wherein said partition and sill are arranged such that a venturi effect is created which increases the velocity and lowers the pressure of the pressurized fluid flowing past said sill.

* * * * *